(12) United States Patent
Choi et al.

(10) Patent No.: US 7,932,368 B2
(45) Date of Patent: Apr. 26, 2011

(54) MULTIPLE SNP FOR DIAGNOSING COLORECTAL CANCER, MICROARRAY AND KIT COMPRISING THE SAME, AND METHOD OF DIAGNOSING COLORECTAL CANCER USING THE SAME

(75) Inventors: Seung-Hak Choi, Seongnam-si (KR); Yun-Sun Nam, Seongnam-si (KR); Jae-Heup Kim, Seoul (KR); Kyu-Sang Lee, Suwon-si (KR); Min-Sun Kim, Hwaseong-si (KR); Tae-Jin Ahn, Seoul (KR)

(73) Assignee: Samsung Electronics Co., Ltd. (KR)

( * ) Notice: Subject to any disclaimer, the term of this patent is extended or adjusted under 35 U.S.C. 154(b) by 517 days.

(21) Appl. No.: 11/909,872

(22) PCT Filed: Apr. 3, 2006

(86) PCT No.: PCT/KR2006/001221
§ 371 (c)(1),
(2), (4) Date: Sep. 17, 2008

(87) PCT Pub. No.: WO2006/104370
PCT Pub. Date: Oct. 5, 2006

(65) Prior Publication Data
US 2009/0215041 A1  Aug. 27, 2009

(30) Foreign Application Priority Data
Apr. 1, 2005 (KR) .................. 10-2005-0027553

(51) Int. Cl.
*C07H 21/04* (2006.01)
*C12Q 1/68* (2006.01)

(52) U.S. Cl. .............. 536/23.1; 435/91.1; 435/91.2; 435/283.1; 435/287.2; 536/24.3

(58) Field of Classification Search .......... None
See application file for complete search history.

(56) References Cited

U.S. PATENT DOCUMENTS
2001/0053519 A1* 12/2001 Fodor et al. ............ 435/6
2007/0128602 A1   6/2007 Park et al.

FOREIGN PATENT DOCUMENTS
WO          2005079173  A2    9/2005

OTHER PUBLICATIONS

NEB catalog (1998/1999), pp. 121, 284.*
EP Extended Search Report; Application No. EP 06732788.2 (EP regional application of PCT/2006001221) dated Dec. 22, 2009.
de la Chapelle, A., Genetic Predisposition to Colorectal Cancer, Nat Rev Cancer, 2004; 4(10): pp. 769-780.
Yeh, C.C. et al., Polymorphisms of the XRCC1, XRCC3, & XPD genes, and colorectal cancer risk: a case-control study in Taiwan, BMC Cancer Jan. 28, 2005; 2005, 5:12.
Goodman, J.E. et al., Arachidonate lipoxygenase (ALOX) and cyclooxygenase (COX) polymorphisms and colon cancer risk, Carcinogenesis 2004, 25(12): pp. 2467-2472.
The International HapMap Project, Nature. Dec. 25, 2003;426 (18): pp. 789-796.
Single Nucleotide Polymorphism; retrieved from NCBI Database Accession No. AFD_CHIP_HYB9; Protocol used for submitted batch ID AFD_EUR_May 18, 2004 submitted to dbSNP Aug. 21, 2004 and comprising SNP rs 1402026; May 25, 2006.
Reference SNP (RefSNP) Cluster Report retrieved from NCBI Database for rs1402026; ss24379070; submitted Aug. 21, 2004.
Single Nucleotide Polymorphism; RefSNP ID: rs1177619; NCBI Assay ID: ss22405697; Aug. 21, 2004.
Single Nucleotide Polymorphism; RefSNP ID: rs2295706; NCBI Assay ID: ss12673809; Aug. 27, 2003.
Single Nucleotide Polymorphism; RefSNP ID: rs1485217; NCBI Assay ID: ss23879382; Aug. 20, 2004.
Single Nucleotide Polymorphism; RefSNP ID: rs1402026; NCBI Assay ID: ss24379070; Aug. 21, 2004.
Single Nucleotide Polymorphism; RefSNP ID: rs1996489; NCBI Assay ID: ss24388388; Aug. 21, 2004.
Kim, J. C., et al.; "Genotyping possible polymorphic variants of human mismatch repair genes in healthy Korean individuals and sporadic colorectal cancer patients"; Familial Cancer; vol. 3; pp. 129-137; 2004.
Haga, H., et al.; "Gene-based SNP discovery as part of the Japanese Millennium Genome Project: identification of 190 562 genetic variations in the human genome"; J. Hum. Genet.; vol. 47; pp. 605-610; 2002.
Gusella, J.F.; "DNA Polymorphism and Human Disease"; Ann. Rev. Biochem. 55:831-854; 1986.

* cited by examiner

*Primary Examiner* — Jeanine A Goldberg
(74) *Attorney, Agent, or Firm* — Cantor Colburn LLP

(57) ABSTRACT

Provided is a multiple single nucleotide polymorphism (SNP) for colorectal cancer diagnosis, a microarray and a kit including a polynucleotide having the SNP, and a method of diagnosing colorectal cancer using the SNP. Early diagnosis of incidence or possibility of colorectal cancer can be effectively performed by using the method.

9 Claims, No Drawings

SEQUENCE LISTING

<160> NUMBER OF SEQ ID NOS: 124

<210> SEQ ID NO 1

```
<211> LENGTH: 201
<212> TYPE: DNA
<213> ORGANISM: Homo sapiens

<400> SEQUENCE: 1
cccaggattg gaaatgatgg atgctttcca ggggccccga tccatcatca gatgaatacg      60 cagcccctc cccaaggaag ctcctggttc attgagatgc ktaattctct ccttatttc      120 attactgttt ctcgtttgta tggattattt ttcttcagta atctgggctt tacatgactg    180
aataagaaaa tcatttgttc a                                               201

<210> SEQ ID NO 2
<211> LENGTH: 201
<212> TYPE: DNA
<213> ORGANISM: Homo sapiens

<400> SEQUENCE: 2
atttcctgcc tgtgataaat gtgtcccaat atttgtcttt tggttgttgt tgttgagaat     60
catttctcat gttgggaaat gtgaagtcaa atagtgtgac wggacttgct gaatgattga   120
gtcaaccaca aatggtattg tcaaccatgg ctgttgaatt aatgagaaca attaaaactc    180
atttttcaga ggtcaaaaga t                                              201

<210> SEQ ID NO 3
<211> LENGTH: 201
<212> TYPE: DNA
<213> ORGANISM: Homo sapiens

<400> SEQUENCE: 3
gccaaatctc cttgagggtc aaatgtgggt aggggagagc tggaggtcag tgatagggta     60
aagggcattc agcaggttca cggctacatt caggggagat ytagaataat cagcagtgcc   120
agctacagaa ggatgggtct gaaagagata gattgctgga gaaattgtaa gagacagtgg   180
tcatctcagg caggaattaa a                                              201

<210> SEQ ID NO 4
<211> LENGTH: 201
<212> TYPE: DNA
<213> ORGANISM: Homo sapiens

<400> SEQUENCE: 4
attagctaaa cagtttaatg atgatctgcc aagaaattga tgtcagcagt tagaaaacta     60
aagtcctttt ttatgcagag acagcacagt tggtaaaatt kttatagttg acaagttgga   120
aagcagtgca tgtctctgac aagacttcag ctctgtggga agtgtttgga agaaatgga    180 gtgatagtgt tgttggcat t                                               201

<210> SEQ ID NO 5
<211> LENGTH: 201
<212> TYPE: DNA
<213> ORGANISM: Homo sapiens

<400> SEQUENCE: 5
attaaaaaac ctgtattttt ggatgtattt ttagaaaaac agatttacag gaaacaaacc     60
aaacaaaaag acttgtggta caagaaaatt agaaaataca ktatatttaa aatgacgtg    120 ttagcttgtc ccaggtaaac tcagttcaaa atatgggata aaagagatt tacttttaac   180 ttcgaacagc tagagaatga t                                              201

<210> SEQ ID NO 6
```

```
<211> LENGTH: 201
<212> TYPE: DNA
<213> ORGANISM: Homo sapiens

<400> SEQUENCE: 6
aagcagaaga tgaccagtct gaggcttcag ggaagaaatc tgtgaaggga gtgtctaaga      60
aatatgttcc tccacgcttg gttccagtac attatggtat raactttggc tgctgcctcc     120
tcagcatgaa ctgtttctct tttctctgtt cttggataac cctgcttatt ttcatcatgt     180
agatgaaaca gaagctgagc g                                                201

<210> SEQ ID NO 7
<211> LENGTH: 201
<212> TYPE: DNA
<213> ORGANISM: Homo sapiens

<400> SEQUENCE: 7
acctggtcta agccaccatc atctctcacc tggattattg catagccccc aaactaacct      60
acctgccttc tcccttgacc ctatttgcaa agaaaaagcc rgagtgatca tgtttaaatg     120
ttgaccagct gatactacct caaggtcttt catcggcttt ccatctcaga acaaaagtaa     180
aggttcttat agtaacctgc c                                                201

<210> SEQ ID NO 8
<211> LENGTH: 201
<212> TYPE: DNA
<213> ORGANISM: Homo sapiens
<220> FEATURE:
<221> NAME/KEY: misc_feature
<222> LOCATION: (128)
<223> OTHER INFORMATION: n at location 128 denotes a or g or c or t

<400> SEQUENCE: 8
ttaattagaa ttagataaat aatactacaa actgagttat ggaaaaaaca tgctacaacg      60
agataagtct cagcacttgc cttttgaaaga acaattgtga rgtattttgc cccatcccaa    120
acccaacngt gatattatat ttgtacagaa aacttactgg ttccaaaact ggattgaact     180
cacttctcct gggtctctag c                                                201

<210> SEQ ID NO 9
<211> LENGTH: 201
<212> TYPE: DNA
<213> ORGANISM: Homo sapiens

<400> SEQUENCE: 9
taagtcgggg agttatgtag ttctatgcat tgtaagttca actagtacaa acaaaattac      60
agtgcttcag tcactactct ctcagtcctt ttctcctccc ygtggttcag taaaagatgg     120
tctcttcttt aagaagtgga aagttttttt tttttttaaac ttttgaagaa accatctctc    180
ctatgctttc cgagaagtga g                                                201

<210> SEQ ID NO 10
<211> LENGTH: 201
<212> TYPE: DNA
<213> ORGANISM: Homo sapiens

<400> SEQUENCE: 10
cagcctgggt gacagagcaa gaagaccctg tttcaaataa aaagggggtgt gatgtgattg     60 caccctagat gacccatggg caagcagtta cacaggtcca ratctgagca cgagtcggat    120
ttatgagtga tcacccaaac agggccgtgc agatgcatgc aatcccctgg atggataccc    180
```

```
cgggcgctca gtgtgcctcc t                                              201
```

<210> SEQ ID NO 11
<211> LENGTH: 201
<212> TYPE: DNA
<213> ORGANISM: Homo sapiens

<400> SEQUENCE: 11

```
cagacaatga cactggtgct gtgtttggac ttgaatcctc cttcacatat tttctgtttg     60
tctccctgat ttatgttctc ttccgtctcc tttcttgctt kcttttgaat caaacacata    120 ttttctttt gcctccttc tgttattggc ttgcgattga tgcattcttt cgatattatg     180
ttagtagcca catatgcttg g                                              201
```

<210> SEQ ID NO 12
<211> LENGTH: 201
<212> TYPE: DNA
<213> ORGANISM: Homo sapiens
<220> FEATURE:
<221> NAME/KEY: misc_feature
<222> LOCATION: (140)
<223> OTHER INFORMATION: n at location 140 denotes a or g or c or t

<400> SEQUENCE: 12

```
catgatcttt attaattgta acatttctac tttggacatt agaactttga aagtcattaa     60
aacccaggcc agagagatgg taagtagaaa tttcttcagt katttatttt gtgtaatcgc    120
ttggagagaa gttttccacn cccagctttt tagttcctga atgtattcta gctataggaa    180
aagtggtaac ataattggct t                                              201
```

<210> SEQ ID NO 13
<211> LENGTH: 201
<212> TYPE: DNA
<213> ORGANISM: Homo sapiens
<220> FEATURE:
<221> NAME/KEY: misc_feature
<222> LOCATION: (56)
<223> OTHER INFORMATION: n at location 56 denotes a or g or c or t

<400> SEQUENCE: 13

```
tgttgctttt cgttaaaaag aacaaagcaa aaagaagaaa catatcaaat gcgaanctcg     60
ttgtgttact tctgtatgat ttcttcttac tctgaattcc yatagcctct tagcccttga    120
cacatatttt cctactttat agtttaaaaa atgccacctg tgtatcttgt ctctttcttt    180
cttctcttcc tctctcatat c                                              201
```

<210> SEQ ID NO 14
<211> LENGTH: 201
<212> TYPE: DNA
<213> ORGANISM: Homo sapiens

<400> SEQUENCE: 14

```
acattcaaaa tgtgagaaca ttaggactta aaatataggc ttggacagaa tcttgatata     60
acatctaact aattcatttg actatatatt gcaaatcttt yacattctaa gtactgaagg    120
gcatccatga actataagat gccttctatc ctcttatgta ctggagctct actttcaggg    180
gaaaatgaaa tgaattcata a                                              201
```

<210> SEQ ID NO 15
<211> LENGTH: 201
<212> TYPE: DNA
<213> ORGANISM: Homo sapiens -continued

```
<400> SEQUENCE: 15
atgtggtgtg cagcatcaca tcacctggaa tttagagtgt caactgctat tttgggagac      60
tctgttgagt cagttttgca aaatggataa aagaattttc kctattgatt ttagtgtttg     120
ttttggtctc cagcagaaat ctcaatcact gaattgcaaa actcttcccc cccagtttat     180
agtagttaat agcatacccaa g                                              201

<210> SEQ ID NO 16
<211> LENGTH: 201
<212> TYPE: DNA
<213> ORGANISM: Homo sapiens

<400> SEQUENCE: 16
gctttcacaa ttacttctac atgaataact tcttatcgca taacctcttt tcatgcctaa      60
gcagttcaga taattcctat gcagtaaaag cactttacat raataatttt atgtcaggct     120
actgagaaat tgaagagcta ttcataggat cttttttacct atcaagtaaa acaattataa    180
ctattctcta aaaaatggaa a                                              201

<210> SEQ ID NO 17
<211> LENGTH: 201
<212> TYPE: DNA
<213> ORGANISM: Homo sapiens
<220> FEATURE:
<221> NAME/KEY: misc_feature
<222> LOCATION: (184)
<223> OTHER INFORMATION: n at location 184 denotes a or g or c or t

<400> SEQUENCE: 17
agaaaccagg ctagggtgtg ctgaggtgcc cagggctccc ctggaaagtc cagacttgga      60
gagggactcc tagggtgtgt ggtgaggggg agaggggtgg sggaccaccc agagcctaga    120
atggatactt ctcagaaaga ctcttgggac gacggaaggg atgaaggaag ggaggtgcag    180
gccnagctga cagctacatt t                                              201

<210> SEQ ID NO 18
<211> LENGTH: 201
<212> TYPE: DNA
<213> ORGANISM: Homo sapiens

<400> SEQUENCE: 18
tggaaaaaga actattcact ttggccatgg gggtcttgtg acaaattagt tcctttggag      60
attgtattca accctgagga atggattaaa cttacaaaaa rtatctataa ctggaccgaa    120
gaatatggaa ggtatgaaca gcagttgtat tttgatgcat ataaacatag cagttttgaa    180
tacccaaaaa aactactaca t                                              201

<210> SEQ ID NO 19
<211> LENGTH: 201
<212> TYPE: DNA
<213> ORGANISM: Homo sapiens
<220> FEATURE:
<221> NAME/KEY: misc_feature
<222> LOCATION: (66)..(129)
<223> OTHER INFORMATION: n at locations 66, 69 and 129 denotes a or g or
      c or t

<400> SEQUENCE: 19
caggtgcaga agttggaaag catgtattga agcaaggctg agacgtctc ctcacttaag      60 aagacntgna atgcgggat ataggacagg agaagtcaaa ragtatgttc agtatggtca    120
tggcttccnt ggggcctgct gtgggatccc agatctaggc tctggaaact gagagaaagg    180
```

```
gacagccctg gtgaggatgg a                                                201
```

\<210\> SEQ ID NO 20
\<211\> LENGTH: 201
\<212\> TYPE: DNA
\<213\> ORGANISM: Homo sapiens
\<220\> FEATURE:
\<221\> NAME/KEY: misc_feature
\<222\> LOCATION: (141)
\<223\> OTHER INFORMATION: n at location 141 denotes a or g or c or t

\<400\> SEQUENCE: 20

```
gttatttta tcagaaatag ccgtaaggtg cagagaggaa acaaaaaagg ggaggcaaga        60
agaattattc tattctatag ttatgccagc caaggtgtat rtattagaac aagactctgg     120
tctttactac actactgtta ncaaggctaa gatcatactg ctgattcaat agtaaaagca     180
cagcttctta agtaagtgtt t                                                201
```

\<210\> SEQ ID NO 21
\<211\> LENGTH: 201
\<212\> TYPE: DNA
\<213\> ORGANISM: Homo sapiens
\<220\> FEATURE:
\<221\> NAME/KEY: misc_feature
\<222\> LOCATION: (126)
\<223\> OTHER INFORMATION: n at location 126 denotes a or g or c or t

\<400\> SEQUENCE: 21

```
agaaaaaacc tggaaataat gcaaatatcc atcaataata gattccaaag tagataaata       60
cattgtggca tatgcatatg atgtgtggga gagagtaaat raattgcagt tagataacca     120
cagaantgaa tgtaaagaac ctaatgctga gtaaaaaaac aaaaactagc tgcaaaagaa     180
aatttatcat atgattccat t                                                201
```

\<210\> SEQ ID NO 22
\<211\> LENGTH: 201
\<212\> TYPE: DNA
\<213\> ORGANISM: Homo sapiens
\<220\> FEATURE:
\<221\> NAME/KEY: misc_feature
\<222\> LOCATION: (86)
\<223\> OTHER INFORMATION: n at location 86 denotes a or g or c or t

\<400\> SEQUENCE: 22

```
tcaagtttaa taggtgctaa gtaaagtctt ttatttccct tctggataat cccctcacca       60
aaccctttca tccagttcaa atgccngggt gctggtgcag ytaggcagac gagaatcatt     120
ctgacagcag agcttaaatg actcaggagt cgctccaatt tcctcatctg gctgccagga     180
tttgtatgga acgtagggta t                                                201
```

\<210\> SEQ ID NO 23
\<211\> LENGTH: 201
\<212\> TYPE: DNA
\<213\> ORGANISM: Homo sapiens
\<220\> FEATURE:
\<221\> NAME/KEY: misc_feature
\<222\> LOCATION: (39)..(79)
\<223\> OTHER INFORMATION: n at locations 39 and 79 denotes a or g or c or
      t

\<400\> SEQUENCE: 23

```
tggaaacaat atccaaacca tactgtgaga ctgcagtana gacttagatg ctaccoctaa       60
atgctggaat cctctgacnc catcgccata aaataagatt mcatgtggca ctcacttcac     120
```

```
gctgcttgct tctgaattga agtcttgctt gggtggacgt gattggcaga ggatgtattg    180
acatgcctgt agcacctggg a                                              201

<210> SEQ ID NO 24
<211> LENGTH: 201
<212> TYPE: DNA
<213> ORGANISM: Homo sapiens

<400> SEQUENCE: 24
ctctattaaa attaaaaaaa gttttaatct cagaatttct atttgattat ttttcaattg    60
tttctagtta cttgcccaaa ttctgcacat taatgtgtaa kttttgaaca ctttgtcatc    120
ctagagagga tttagttttg tttgttttag gtagtcaggc cagggtcagg taattttaat    180
ataatcatga tttgagctga c                                              201

<210> SEQ ID NO 25
<211> LENGTH: 201
<212> TYPE: DNA
<213> ORGANISM: Homo sapiens

<400> SEQUENCE: 25
cctgttaaac aagatcattt tgtcttctga taaagtgcaa gcctttgtac tcaagcttat    60
atttttaggt ggccttatgt taaatgagag tgaataggct raataagttg agaaacaaag    120
caaacttgag acttgggtct agaaaaagaa aactaagtga ggtcactgta atatagacat    180
ttctagaagc aaacagatca g                                              201

<210> SEQ ID NO 26
<211> LENGTH: 201
<212> TYPE: DNA
<213> ORGANISM: Homo sapiens

<400> SEQUENCE: 26
agctctcatg cggcccccag agatcccaaa acccgcagcc tggttctgtg gatctgaagg    60
caccattctc tgccctgagt agccatggag aagcccctca magccaccca ggccacctgg    120
ccttcggatg gggtcttgct gctgggccac ggcctggggg acaccaggcc ctcctcagcg    180
agcgctcagc gctcaccctg t                                              201

<210> SEQ ID NO 27
<211> LENGTH: 201
<212> TYPE: DNA
<213> ORGANISM: Homo sapiens

<400> SEQUENCE: 27
agatgtctca gacagtaagt taacaaaagc gtttttctag gacgaatgta ggacctcaaa    60
ggctgggcat cccagcagtg cagcgtggaa gacagacccg sgattgcaca caggctggga    120
gccacagggc ctgcacccct cccagaactg attgatcccc tcgttgagtg ctcggtggcc    180
ccctcggtgg tatgcgggtc c                                              201

<210> SEQ ID NO 28
<211> LENGTH: 201
<212> TYPE: DNA
<213> ORGANISM: Homo sapiens
<220> FEATURE:
<221> NAME/KEY: misc_feature
<222> LOCATION: (13)
<223> OTHER INFORMATION: n at location 13 denotes a or g or c or t

<400> SEQUENCE: 28
```

```
gcaggatgaa ttnttttact tattcatatg atcataacaa atattcaaaa attacgccaa        60
caaatctttc cattcctttc cattccctct gcaagaataa matcaaataa ctgttaggct       120
ataaacaaca ttaaagtatt tattttcccc ctataaatgt gaaaggacag ggataattaa       180
cttggtgcag aaactatgtt t                                                 201

<210> SEQ ID NO 29
<211> LENGTH: 201
<212> TYPE: DNA
<213> ORGANISM: Homo sapiens

<400> SEQUENCE: 29
aactatataa aatccagtgg tcacagtttt gctgcttctt ccatcttgat cctcatttta        60
tattccctat atataaagtt tgagtgtgtg cgtgtgtgtt wgagacatca aaagtttcaa       120
aaaactagtt tctcagtctt tggagggtca ggtagctaag aaaccaagac atccagcctt       180
taaaggtacc tcctaaaatc t                                                 201

<210> SEQ ID NO 30
<211> LENGTH: 201
<212> TYPE: DNA
<213> ORGANISM: Homo sapiens

<400> SEQUENCE: 30
ctttggcata tcaatcctga ttccaaattt tgcatcttaa aaactggaaa ttaaaaatgt        60
gtattcaaat atccatttga ctgcttccca ttaaaagtta mattttacag caacaaaatt       120
gtgttgcata tagtatatac atatcaaaat aaaacatatt tgccaacttt atcatttctt       180
ttcctaatcc tgattctgta t                                                 201

<210> SEQ ID NO 31
<211> LENGTH: 201
<212> TYPE: DNA
<213> ORGANISM: Homo sapiens
<220> FEATURE:
<221> NAME/KEY: misc_feature
<222> LOCATION: (84)
<223> OTHER INFORMATION: n at location 84 denotes a or g or c or t

<400> SEQUENCE: 31
ccgagaatgt tacttatacc aagttatgga agatgagtgt tatggcctga attccccca         60 aaagatgata tgttaaagcc tacnccccag aaacccagaa wtggctgtat ttgaagatcg       120
ggtctttaca gaagtaatga agttaaaatg gggtcatatg ggtgggcctc agtccagtct       180
aactgtgtcc ctgtaagaag a                                                 201

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
acgttggatg aaggaagctc ctggttcatt                                         30

<210> SEQ ID NO 33
<211> LENGTH: 30
<212> TYPE: DNA
<213> ORGANISM: Artificial Sequence
<220> FEATURE:
<223> OTHER INFORMATION: primer
```

```
<400> SEQUENCE: 33
acgttggatg tccatacaaa cgagaaacag                                    30

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ctcctggttc attgagatgc                                               20

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
acgttggatg ggttgactca atcattcagc                                    30

<210> SEQ ID NO 36
<211> LENGTH: 31
<212> TYPE: DNA
<213> ORGANISM: Artificial Sequence
<220> FEATURE:
<223> OTHER INFORMATION: primer

<400> SEQUENCE: 36
acgttggatg ctcatgttgg gaaatgtgaa g                                  31

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
actcaatcat tcagcaagtc c                                             21

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
acgttggatg ctctttcaga cccatccttc                                    30

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
acgttggatg aggttcacgg ctacattcag                                    30

<210> SEQ ID NO 40
<211> LENGTH: 21
<212> TYPE: DNA
```

```
<213> ORGANISM: Artificial Sequence
<220> FEATURE:
<223> OTHER INFORMATION: primer

<400> SEQUENCE: 40
ctggcactgc tgattattct a                                             21

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
acgttggatg atgcagagac agcacagttg                                    30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
acgttggatg gtcttgtcag agacatgcac                                    30

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
agacagcaca gttggtaaaa tt                                            22

<210> SEQ ID NO 44
<211> LENGTH: 30
<212> TYPE: DNA
<213> ORGANISM: Artificial Sequence
<220> FEATURE:
<223> OTHER INFORMATION: priemr

<400> SEQUENCE: 44
acgttggatg tttacctggg acaagctaac                                    30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
acgttggatg ccaaacaaaa agacttgtgg                                    30

<210> SEQ ID NO 46
<211> LENGTH: 24
<212> TYPE: DNA
<213> ORGANISM: Artificial Sequence
<220> FEATURE:
<223> OTHER INFORMATION: primer

<400> SEQUENCE: 46
gctaacacgt ccattttaaa tata                                          24
```

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
acgttggatg agaaatatgt tcctccacgc                                    30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
acgttggatg aacagttcat gctgaggagg                                    30

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
ggttccagta cattatggta t                                             21

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
acgttggatg gaccttgagg tagtatcagc                                    30

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
acgttggatg ccttgaccct atttgcaaag                                    30

<210> SEQ ID NO 52
<211> LENGTH: 23
<212> TYPE: DNA
<213> ORGANISM: Artificial Sequence
<220> FEATURE:
<223> OTHER INFORMATION: primer

<400> SEQUENCE: 52
tcaacattta aacatgatca ctc                                           23

<210> SEQ ID NO 53
<211> LENGTH: 30
<212> TYPE: DNA
<213> ORGANISM: Artificial Sequence
<220> FEATURE:
<223> OTHER INFORMATION: primer

```
<400> SEQUENCE: 53
acgttggatg ccagttttgg aaccagtaag                                    30

<210> SEQ ID NO 54
<211> LENGTH: 30
<212> TYPE: DNA
<213> ORGANISM: Artificial Sequence
<220> FEATURE:
<223> OTHER INFORMATION: primer

<400> SEQUENCE: 54
acgttggatg gcacttgcct ttgaaagaac                                    30

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55
ttgggatggg gcaaaatac                                                19

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
acgttggatg cagtgcttca gtcactactc                                    30

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57
acgttggatg ccacttctta aagaagagac c                                  31

<210> SEQ ID NO 58
<211> LENGTH: 17
<212> TYPE: DNA
<213> ORGANISM: Artificial Sequence
<220> FEATURE:
<223> OTHER INFORMATION: primer

<400> SEQUENCE: 58 agtcctttc tcctccc                                                   17

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
acgttggatg tgattgcacc ctagatgacc                                    30

<210> SEQ ID NO 60
<211> LENGTH: 30
<212> TYPE: DNA
```

```
<213> ORGANISM: Artificial Sequence
<220> FEATURE:
<223> OTHER INFORMATION: primer

<400> SEQUENCE: 60
acgttggatg ctcataaatc cgactcgtgc                                    30

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
caagcagtta cacaggtcca                                               20

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
acgttggatg gttctcttcc gtctcctttc                                    30

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
acgttggatg gcaagccaat aacagaaggg                                    30

<210> SEQ ID NO 64
<211> LENGTH: 17
<212> TYPE: DNA
<213> ORGANISM: Artificial Sequence
<220> FEATURE:
<223> OTHER INFORMATION: primer

<400> SEQUENCE: 64
cgtctccttt cttgctt                                                  17

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
acgttggatg ttaaaaccca ggccagagag                                    30

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
acgttggatg ggaaaacttc tctccaagcg                                    30
```

```
<210> SEQ ID NO 67
<211> LENGTH: 22
<212> TYPE: DNA
<213> ORGANISM: Artificial Sequence
<220> FEATURE:
<223> OTHER INFORMATION: primer

<400> SEQUENCE: 67
ggtaagtaga aatttcttca gt                                          22

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
acgttggatg ggaaaatatg tgtcaagggc                                  30

<210> SEQ ID NO 69
<211> LENGTH: 30
<212> TYPE: DNA
<213> ORGANISM: Artificial Sequence
<220> FEATURE:
<223> OTHER INFORMATION: primer

<400> SEQUENCE: 69
acgttggatg cgttgtgtta cttctgtatg                                  30

<210> SEQ ID NO 70
<211> LENGTH: 17
<212> TYPE: DNA
<213> ORGANISM: Artificial Sequence
<220> FEATURE:
<223> OTHER INFORMATION: primer

<400> SEQUENCE: 70
aagggctaag aggctat                                                17

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
acgttggatg agttcatgga tgcccttcag                                  30

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
acgttggatg taggcttgga cagaatcttg                                  30

<210> SEQ ID NO 73
<211> LENGTH: 20
<212> TYPE: DNA
<213> ORGANISM: Artificial Sequence
<220> FEATURE:
<223> OTHER INFORMATION: primer
```

```
<400> SEQUENCE: 73
cccttcagta cttagaatgt                                              20

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
acgttggatg ctctgttgag tcagttttgc                                   30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
acgttggatg tgagatttct gctggagacc                                   30

<210> SEQ ID NO 76
<211> LENGTH: 24
<212> TYPE: DNA
<213> ORGANISM: Artificial Sequence
<220> FEATURE:
<223> OTHER INFORMATION: primer

<400> SEQUENCE: 76
tgcaaaatgg ataaaagaat tttc                                         24

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
acgttggatg ttcatgccta agcagttcag                                   30

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
acgttggatg caatttctca gtagcctgac                                   30

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
gcagtaaaag cactttacat                                              20

<210> SEQ ID NO 80
<211> LENGTH: 30
<212> TYPE: DNA
```

```
<213> ORGANISM: Artificial Sequence
<220> FEATURE:
<223> OTHER INFORMATION: primer

<400> SEQUENCE: 80
acgttggatg tatccattct aggctctggg                                    30

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
acgttggatg gaaagtccag acttggagag                                    30

<210> SEQ ID NO 82
<211> LENGTH: 18
<212> TYPE: DNA
<213> ORGANISM: Artificial Sequence
<220> FEATURE:
<223> OTHER INFORMATION: primer

<400> SEQUENCE: 82
ctaggctctg ggtggtcc                                                 18

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
acgttggatg ggagattgta ttcaaccctg                                    30

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
acgttggatg ccttccatat tcttcggtcc                                    30

<210> SEQ ID NO 85
<211> LENGTH: 23
<212> TYPE: DNA
<213> ORGANISM: Artificial Sequence
<220> FEATURE:
<223> OTHER INFORMATION: primer

<400> SEQUENCE: 85
ggaatggatt aaacttacaa aaa                                           23

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
acgttggatg aatggcggga tataggacag                                    30
```

```
<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
acgttggatg tagatctggg atcccacagc                                    30

<210> SEQ ID NO 88
<211> LENGTH: 17
<212> TYPE: DNA
<213> ORGANISM: Artificial Sequence
<220> FEATURE:
<223> OTHER INFORMATION: primer

<400> SEQUENCE: 88
ggacaggaga agtcaaa                                                  17

<210> SEQ ID NO 89
<211> LENGTH: 30
<212> TYPE: DNA
<213> ORGANISM: Artificial Sequence
<220> FEATURE:
<223> OTHER INFORMATION: primer

<400> SEQUENCE: 89
acgttggatg ctatagttat gccagccaag                                    30

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
acgttggatg gcagtatgat cttagccttg                                    30

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
ttatgccagc caaggtgtat                                               20

<210> SEQ ID NO 92
<211> LENGTH: 30
<212> TYPE: DNA
<213> ORGANISM: Artificial Sequence
<220> FEATURE:
<223> OTHER INFORMATION: primer

<400> SEQUENCE: 92
acgttggatg gcatatgatg tgtgggagag                                    30

<210> SEQ ID NO 93
<211> LENGTH: 30
<212> TYPE: DNA
<213> ORGANISM: Artificial Sequence
<220> FEATURE:
<223> OTHER INFORMATION: primer
```

```
<400> SEQUENCE: 93
acgttggatg ctcagcatta ggttctttac                                  30

<210> SEQ ID NO 94
<211> LENGTH: 18
<212> TYPE: DNA
<213> ORGANISM: Artificial Sequence
<220> FEATURE:
<223> OTHER INFORMATION: primer

<400> SEQUENCE: 94
gtgtgggaga gagtaaat                                               18

<210> SEQ ID NO 95
<211> LENGTH: 30
<212> TYPE: DNA
<213> ORGANISM: Artificial Sequence
<220> FEATURE:
<223> OTHER INFORMATION: primer

<400> SEQUENCE: 95
acgttggatg tgctgtcaga atgattctcg                                  30

<210> SEQ ID NO 96
<211> LENGTH: 30
<212> TYPE: DNA
<213> ORGANISM: Artificial Sequence
<220> FEATURE:
<223> OTHER INFORMATION: primer

<400> SEQUENCE: 96
acgttggatg cctcaccaaa ccctttcatc                                  30

<210> SEQ ID NO 97
<211> LENGTH: 17
<212> TYPE: DNA
<213> ORGANISM: Artificial Sequence
<220> FEATURE:
<223> OTHER INFORMATION: primer

<400> SEQUENCE: 97
tgattctcgt ctgccta                                                17

<210> SEQ ID NO 98
<211> LENGTH: 30
<212> TYPE: DNA
<213> ORGANISM: Artificial Sequence
<220> FEATURE:
<223> OTHER INFORMATION: primer

<400> SEQUENCE: 98
acgttggatg caattcagaa gcaagcagcg                                  30

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
acgttggatg ccctaaatgc tggaatcctc                                  30

<210> SEQ ID NO 100
<211> LENGTH: 17
<212> TYPE: DNA
```

<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 100
gaagtgagtg ccacatg                                                17

<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 101
acgttggatg tacttgccca aattctgcac                                  30

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
acgttggatg ctggcctgac tacctaaaac                                  30

<210> SEQ ID NO 103
<211> LENGTH: 22
<212> TYPE: DNA
<213> ORGANISM: Artificial Sequence
<220> FEATURE:
<223> OTHER INFORMATION: primer

<400> SEQUENCE: 103
aattctgcac attaatgtgt aa                                          22

<210> SEQ ID NO 104
<211> LENGTH: 31
<212> TYPE: DNA
<213> ORGANISM: Artificial Sequence
<220> FEATURE:
<223> OTHER INFORMATION: primer

<400> SEQUENCE: 104
acgttggatg ggtggcctta tgttaaatga g                                31

<210> SEQ ID NO 105
<211> LENGTH: 30
<212> TYPE: DNA
<213> ORGANISM: Artificial Sequence
<220> FEATURE:
<223> OTHER INFORMATION: primer

<400> SEQUENCE: 105
acgttggatg gacccaagtc tcaagttttgc                                 30

<210> SEQ ID NO 106
<211> LENGTH: 19
<212> TYPE: DNA
<213> ORGANISM: Artificial Sequence
<220> FEATURE:
<223> OTHER INFORMATION: primer

<400> SEQUENCE: 106
aaatgagagt gaataggct                                              19

```
<210> SEQ ID NO 107
<211> LENGTH: 30
<212> TYPE: DNA
<213> ORGANISM: Artificial Sequence
<220> FEATURE:
<223> OTHER INFORMATION: primer

<400> SEQUENCE: 107
acgttggatg cagcaagacc ccatccgaag                                        30

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
acgttggatg tctgaaggca ccattctctg                                        30

<210> SEQ ID NO 109
<211> LENGTH: 17
<212> TYPE: DNA
<213> ORGANISM: Artificial Sequence
<220> FEATURE:
<223> OTHER INFORMATION: primer

<400> SEQUENCE: 109
aggtggcctg ggtggct                                                      17

<210> SEQ ID NO 110
<211> LENGTH: 30
<212> TYPE: DNA
<213> ORGANISM: Artificial Sequence
<220> FEATURE:
<223> OTHER INFORMATION: primer

<400> SEQUENCE: 110
acgttggatg atcaatcagt tctgggaggg                                        30

<210> SEQ ID NO 111
<211> LENGTH: 30
<212> TYPE: DNA
<213> ORGANISM: Artificial Sequence
<220> FEATURE:
<223> OTHER INFORMATION: primer

<400> SEQUENCE: 111
acgttggatg agcagtgcag cgtggaagac                                        30

<210> SEQ ID NO 112
<211> LENGTH: 17
<212> TYPE: DNA
<213> ORGANISM: Artificial Sequence
<220> FEATURE:
<223> OTHER INFORMATION: primer

<400> SEQUENCE: 112
ccagcctgtg tgcaatc                                                      17

<210> SEQ ID NO 113
<211> LENGTH: 30
<212> TYPE: DNA
<213> ORGANISM: Artificial Sequence
<220> FEATURE:
<223> OTHER INFORMATION: primer
```

<400> SEQUENCE: 113
acgttggatg cctttccatt ccctctgcaa                                              30

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
acgttggatg gtcctttcac atttataggg                                              30

<210> SEQ ID NO 115
<211> LENGTH: 21
<212> TYPE: DNA
<213> ORGANISM: Artificial Sequence
<220> FEATURE:
<223> OTHER INFORMATION: primer

<400> SEQUENCE: 115
ccattccctc tgcaagaata a                                                       21

<210> SEQ ID NO 116
<211> LENGTH: 30
<212> TYPE: DNA
<213> ORGANISM: Artificial Sequence
<220> FEATURE:
<223> OTHER INFORMATION: primer

<400> SEQUENCE: 116
acgttggatg aaagtttgag tgtgtgcgtg                                              30

<210> SEQ ID NO 117
<211> LENGTH: 30
<212> TYPE: DNA
<213> ORGANISM: Artificial Sequence
<220> FEATURE:
<223> OTHER INFORMATION: primer

<400> SEQUENCE: 117
acgttggatg ccctccaaag actgagaaac                                              30

<210> SEQ ID NO 118
<211> LENGTH: 19
<212> TYPE: DNA
<213> ORGANISM: Artificial Sequence
<220> FEATURE:
<223> OTHER INFORMATION: primer

<400> SEQUENCE: 118
gagtgtgtgc gtgtgtgtt                                                          19

<210> SEQ ID NO 119
<211> LENGTH: 30
<212> TYPE: DNA
<213> ORGANISM: Artificial Sequence
<220> FEATURE:
<223> OTHER INFORMATION: primer

<400> SEQUENCE: 119
acgttggatg tcaaatatcc atttgactgc                                              30

<210> SEQ ID NO 120
<211> LENGTH: 30
<212> TYPE: DNA

```
-continued

<213> ORGANISM: Artificial Sequence
<220> FEATURE:
<223> OTHER INFORMATION: primer

<400> SEQUENCE: 120
acgttggatg gcaacacaat tttgttgctg                                    30

<210> SEQ ID NO 121
<211> LENGTH: 21
<212> TYPE: DNA
<213> ORGANISM: Artificial Sequence
<220> FEATURE:
<223> OTHER INFORMATION: primer

<400> SEQUENCE: 121
actgcttccc attaaaagtt a                                             21

<210> SEQ ID NO 122
<211> LENGTH: 30
<212> TYPE: DNA
<213> ORGANISM: Artificial Sequence
<220> FEATURE:
<223> OTHER INFORMATION: primer

<400> SEQUENCE: 122
acgttggatg tctgtaaaga cccgatcttc                                    30

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
acgttggatg tgttatggcc tgaattcccc                                    30

<210> SEQ ID NO 124
<211> LENGTH: 18
<212> TYPE: DNA
<213> ORGANISM: Artificial Sequence
<220> FEATURE:
<223> OTHER INFORMATION: primer

<400> SEQUENCE: 124
gatcttcaaa tacagcca                                                 18
```

US 7,932,368 B2

MULTIPLE SNP FOR DIAGNOSING COLORECTAL CANCER, MICROARRAY AND KIT COMPRISING THE SAME, AND METHOD OF DIAGNOSING COLORECTAL CANCER USING THE SAME

CROSS-REFERENCE TO RELATED PATENT APPLICATION

This application is a 371 national stage application of International Application No. PCT/KR2006/001221, filed Apr. 3, 2006, which claims priority to Korean Patent Application No. 10-2005-0027553, filed on Apr. 1, 2005, the disclosure of which is incorporated herein in its entirety by reference.

BACKGROUND OF THE INVENTION

1. Field of the Invention

The present invention relates to a multiple single nucleotide polymorphism (SNP) for diagnosing colorectal cancer, a microarray and a kit including the same, and a method of diagnosing colorectal cancer using the same.

2. Description of the Related Art

The genomes of all organisms undergo spontaneous mutation in the course of their continuing evolution, generating variant forms of progenitor nucleic acid sequences (Gusella, *Ann. Rev. Biochem.* 55, 831-854, 1986). The variant forms of progenitor nucleic acid sequences may confer an evolutionary advantage or disadvantage, or may be neutral relative to a progenitor form. In some instances, a variant form confers a lethal disadvantage and is not transmitted to subsequent generations of the organism. In other instances, a variant form confers an evolutionary advantage to the species and is eventually incorporated into the DNA of most members of the species and effectively becomes the progenitor form. In many instances, both progenitor and a variant forms survive and coexist in a species population. The coexistence of multiple forms of a sequence gives rise to polymorphisms.

Several types of polymorphisms are known, including restriction fragment length polymorphism (RFLP), short tandem repeats (STR) and single nucleotide polymorphism (SNP). Among them, SNPs take the form of single nucleotide variations among individuals of the same species. When SNPs occur in protein coding sequences, some of the polymorphic forms may give rise to the non-synonymous change of amino acid causing expression of a defective or a variant protein. On the other hand, when a SNP occurs in non-coding sequences, some of these polymorphisms may cause the expression of defective or variant proteins as a result of defective splicing, for example. Other SNPs have no phenotypic effect.

It is estimated that human SNPs occur at a frequency of 1 in every 1,000 bp. When such SNPs induce a phenotypic expression such as a disease, polynucleotides containing the SNPs can be used as a primer or a probe for diagnosis of the disease. Monoclonal antibodies specifically binding with the SNPs can also be used in the diagnosis of the disease. Currently, research into the nucleotide sequences and functions of SNPs is being performed by many research institutes. The nucleotide sequences and the results of other experiments on the identified human SNPs have been put in databases to be easily accessible.

Even though findings available to date show that specific SNPs exist in human genomes or cDNAs, the phenotypic effects of SNP's have not been revealed. Functions of most SNPs have not yet been discovered.

Most colorectal cancers are pathologically adenocarcinoma and roughly divided into colon cancer and rectal cancer according to the region in which the cancer occurs. The incidence of rectal cancer is highest at about 50%. According to recent research, the incidence of colorectal cancer and the death rate due to colorectal cancer are significantly increasing in Korea due to eating habit changes. The incidence of colorectal cancer increased by 420% from 1995 to 2002 and was the most common type of cancer (2003's Health insurance statistics, Korean National Health Insurance Corporation).

Causes of colorectal cancer are not clearly revealed, but genetic factors, eating habits related to high fat and low fiber diets, and inflammatory bowel disease are contributory factors. Colorectal cancer can occur in all age groups. As age increases, the incidence of colorectal cancer increases, and the 50-70 age bracket has a high incidence. Colon cancer often occurs in females and rectal cancer often occurs in males.

Treatment of colorectal cancer is based on surgical excision, which is performed in parallel with cancer chemotherapy and radiation therapy. In spite of the advancement of surgical therapy, cancer chemotherapy and radiation therapy, a dramatic improvement in prognosis is not achieved once the cancer has occurred. The average five-year survival rate is 90% or more for stage I, 70% or more for stage II, 50% or more for stage III, and 5% or less for stage IV (Information for Cancer, 2004, National Cancer Center).

As described above, when colorectal cancer is early detected and treated, accordingly the survival rate is significantly increased. Thus, early diagnosis of colorectal cancer is urgently required. The diagnosis of colorectal cancer is performed by rectal digital examination, stool occult blood examination, and barium enema for patients that have colorectal disease-related symptoms. If necessary, histologic examination through sigmoidoscopy and colonoscopy is performed.

However, conventional methods as described above have low diagnostic accuracy, cannot early diagnose colorectal cancer before it occurs, and are uncomfortable for the subject being examined.

Intensive investigations made by the present inventors in view of the above existing circumstances have resulted in finding that all individuals having colorectal cancer have the same specific SNPs, and the SNPs make it possible to predict the incidence probability of and genetic susceptibility to colorectal cancer, and have come to complete the present invention.

SUMMARY OF THE INVENTION

The present invention provides a multiple single nucleotide polymorphism (SNP) for colorectal cancer diagnosis.

The present invention also provides a polynucleotide hybridized with the polynucleotide of the multiple SNP.

The present invention also provides a microarray for colorectal cancer diagnosis including the polynucleotide, a polypeptide encoded by the polynucleotide and cDNA thereof.

The present invention also provides a kit for colorectal cancer diagnosis including the microarray.

The present invention also provides a method of diagnosing colorectal cancer using the multiple SNP.

According to an aspect of the present invention, there is provided a multiple SNP for colorectal cancer diagnosis including one or more polynucleotides among nucleotide sequences of SEQ ID NOS: 1 to 31, each of which includes at least 10 contiguous bases and the 101st base, and complementary polynucleotides of the nucleotide sequences.

According to another aspect of the present invention, there is provided a polynucleotide hybridized with the polynucleotide and complementary polynucleotides of the nucleotide sequences.

According to another aspect of the present invention, there is provided a microarray for colorectal cancer diagnosis including the polynucleotide, the complementary polynucleotides of the nucleotide sequences, the polynucleotide hybridized with one of the polynucleotides, polypeptide encoded by one of the polynucleotides or cDNA thereof.

According to another aspect of the present invention, there is provided a kit for colorectal cancer diagnosis including the microarray.

According to another aspect of the present invention, there is provided a method for diagnosing colorectal cancer including isolating a DNA from a subject to be diagnosed; determining a base sequence at a SNP site of the DNA; and judging that the subject has colorectal cancer or has a high incidence probability of colorectal cancer.

The above aspects and advantages of the present invention will become more apparent by describing in detail exemplary embodiments thereof.

DETAILED DESCRIPTION OF THE INVENTION

A multiple single nucleotide polymorphism (SNP) for colorectal cancer diagnosis according to an embodiment of the present invention includes one or more polynucleotides among nucleotide sequences of SEQ ID NOS: 1 to 31, each of which includes at least 10 contiguous bases and the 101st base, and complementary polynucleotides of the nucleotide sequences.

TABLE 1

| GenBank accession No. of SNP in NCBI | Polynucleotide containing SNP |
|---|---|
| rs1402026 | SEQ ID NO: 1 |
| rs1485217 | SEQ ID NO: 2 |
| rs1177619 | SEQ ID NO: 3 |
| rs1996489 | SEQ ID NO: 4 |
| rs1334856 | SEQ ID NO: 5 |
| rs2295706 | SEQ ID NO: 6 |
| rs158240 | SEQ ID NO: 7 |
| rs1191354 | SEQ ID NO: 8 |
| rs1028586 | SEQ ID NO: 9 |
| rs317913 | SEQ ID NO: 10 |
| rs1486945 | SEQ ID NO: 11 |

TABLE 1-continued

| GenBank accession No. of SNP in NCBI | Polynucleotide containing SNP |
|---|---|
| rs1025882 | SEQ ID NO: 12 |
| rs1511045 | SEQ ID NO: 13 |
| rs954881 | SEQ ID NO: 14 |
| rs731132 | SEQ ID NO: 15 |
| rs1901223 | SEQ ID NO: 16 |
| rs1182477 | SEQ ID NO: 17 |
| rs1041316 | SEQ ID NO: 18 |
| rs1416095 | SEQ ID NO: 19 |
| rs1020922 | SEQ ID NO: 20 |
| rs1583697 | SEQ ID NO: 21 |
| Rs992922 | SEQ ID NO: 22 |
| rs566419 | SEQ ID NO: 23 |
| rs1877290 | SEQ ID NO: 24 |
| rs9875627 | SEQ ID NO: 25 |
| rs1741621 | SEQ ID NO: 26 |
| rs310606 | SEQ ID NO: 27 |
| rs1504299 | SEQ ID NO: 28 |
| rs12632390 | SEQ ID NO: 29 |
| rs1408889 | SEQ ID NO: 30 |
| rs225403 | SEQ ID NO: 31 |

The SNP may be the most commonly found single base-pair variation among DNA sequence polymorphisms shown in every 1 kb in the DNA of individuals.

A multiple SNP for colorectal cancer diagnosis may be any one of Nos. 1 through 14 in Table 2 as a combination of one or more polynucleotides among nucleotide sequences of SEQ ID NOS: 1 to 31, each of which includes at least 10 contiguous bases and the 101st base.

TABLE 2

| No. | Multiple SNP marker |
|---|---|
| 1 | (rs1402026, rs1177619, rs1191354, rs731132) |
| 2 | (rs1402026, rs1177619, rs1486945, rs1025882) |
| 3 | (rs1402026, rs1177619, rs1191354, rs1025882) |
| 4 | (rs1177619, rs158240, rs992922, rs9875627) |
| 5 | (rs1485217, rs1025882, rs731132, rs1182477) |
| 6 | (rs1485217, rs158240, rs1416095, rs225403) |
| 7 | (rs1485217, rs1486945, rs1020922, rs1504299) |
| 8 | (rs1485217, rs158240, rs317913, rs1583697) |
| 9 | (rs1402026, rs1511045, rs1182477, rs1041316) |
| 10 | (rs1996489, rs1028586, rs954881, rs310606) |
| 11 | (rs1334856, rs1511045, rs566419, rs1741621) |
| 12 | (rs158240, rs1511045, rs1877290, rs1504299) |
| 13 | (rs2295706, rs954881, rs9875627, rs12632390) |
| 14 | (rs1191354, rs1901223, rs1877290, rs1408889) |

In the multiple SNP for colorectal cancer diagnosis, allele of the 101st base of the selected polynucleotides may have a genotype in Table 3.

TABLE 3

| No. | Multiple SNP | Allele genotype |
|---|---|---|
| 1 | (rs1402026, re1177619, rs1191354, rs731132) | (TG or GG, TT, GG or GA, TT or TG) |
| 2 | (rs1402026, rs1177619, rs1486945, rs1025882) | (TG or GG, TT, TG or GG, TT or TG) |
| 3 | (rs1402026, rs1177619, rs1191354, rs1025882) | (TG or GG, TT, GG or GA, TT or TG) |
| 4 | (rs1177619, rs158240, rs992922, rs9875627) | (TT, GG or GA, TT or TC, GG) |
| 5 | (rs1485217, rs1025882, rs731132, rs1182477) | (TT, TG or GG, TT or TG, GC or CC) |
| 6 | (rs1485217, rs158240, rs1416095, rs225403) | (TT, GG or GA, AG r GG, AT or TT) |
| 7 | (rs1485217, rs1486945, rs1020922, rs1504299) | (TT, TG or GG, AA or AG, CC) |
| 8 | (rs1485217, rs158240, rs317913, rs1583697) | (TT, GA or AA, AA or AG, AG or GG) |
| 9 | (rs1402026, rs1511045, rs1182477, rs1041316) | (TG or GG, CC, GC, AG or GG) |
| 10 | (rs1996489, rs1028586, rs954881, rs310606) | (TG or GG, CT, TC or CC, GC or CC) |
| 11 | (rs1334856, rs1511045, rs566419, rs1741621) | (GG or GT, CC, CC, AC) |
| 12 | (rs158240, rs1511045, rs1877290, rs1504299) | (GA, CC, TT, CC) |
| 13 | (rs2295706, rs954881, rs9875627, rs12632390) | (AA or AG, TC or CC, GG, TA) |
| 14 | (rs1191354, rs1901223, rs1877290, rs1408889) | (GA, AA or AG, TT, CC or CA) |

The GenBank accession No. of an SNP in the National Center for Biotechnology Information (NCBI) database indicates a sequence and a position of the SNP. Those skilled in the art may easily identify the sequence and the position of the SNP using the GenBank accession No. The specific sequences corresponding to the rs No. of the SNP registered in NCBI may change over time. It is obvious to those skilled in the art that the sequences are within the scope of the present invention, even if the corresponding rs number changes. The nucleotide sequences of SEQ ID NOS: 1 to 31 are also polynucleotides including the base sequences of SNPs (each $101^{st}$ position), i.e., rs1402026, rs1485217, rs1177619, rs1996489, rs1334856, rs2295706, rs158240, rs1191354, rs1028586, rs317913, rs1486945, rs1025882, rs1511045, rs954881, rs731132, rs1901223, rs1182477, rs1041316, rs1416095, rs1020922, rs1583697, rs992922, rs566419, rs1877290, rs9875627, rs1741621, rs310606, rs1504299, rs12632390, rs1408889 and rs225403. The characteristics of the polynucleotides and the SNPs of the polynucleotides are described in Table 4.

The nucleotide sequences of SEQ ID NOS: 1 to 31 are polymorphic sequences. A polymorphic sequence is a polynucleotide sequence including a polymorphic site representing a SNP. The polynucleotide sequences can be DNA or RNA.

The multiple SNP of the present embodiment is selected from single SNPs set forth in Table 1, i.e., polynucleotides of SEQ ID NOS: 1 to 31, each of which includes at least 10 contiguous bases and the 101st base

TABLE 4

| GenBank accession No. of SNP in NCBI | Polynucleotide containing SNP | Involved No. in multiple SNP combination | Gene | SNP function | No. of chromosome |
|---|---|---|---|---|---|
| rs1402026 | SEQ ID NO: 1 | 4 | Between genes | Between genes | 5 |
| rs1485217 | SEQ ID NO: 2 | 4 | Between genes | Between genes | 3 |
| rs1177619 | SEQ ID NO: 3 | 3 | Between genes | Between genes | 6 |
| rs1996489 | SEQ ID NO: 4 | 1 | Between genes | Between genes | 3 |
| rs1334856 | SEQ ID NO: 5 | 1 | Between genes | Between genes | 13 |
| rs2295706 | SEQ ID NO: 6 | 1 | C14 orf120 | Intron | 14 |
| rs158240 | SEQ ID NO: 7 | 4 | Between genes | Between genes | 5 |
| rs1191354 | SEQ ID NO: 8 | 3 | Between genes | Between genes | 14 |
| rs1028586 | SEQ ID NO: 9 | 1 | C14 orf120 | Intron | 14 |
| rs317913 | SEQ ID NO: 10 | 1 | RGL3 | Intron | 19 |
| rs1486945 | SEQ ID NO: 11 | 2 | Between genes | Between genes | 5 |
| rs1025882 | SEQ ID NO: 12 | 3 | Between genes | Between genes | 18 |
| rs1511045 | SEQ ID NO: 13 | 3 | Between genes | Between genes | 4 |
| rs954881 | SEQ ID NO: 14 | 2 | Between genes | Between genes | 14 |
| rs731132 | SEQ ID NO: 15 | 2 | OR2B2 | Promoter | 6 |
| rs1901223 | SEQ ID NO: 16 | 1 | LPHN3 | Intron | 4 |
| rs1182477 | SEQ ID NO: 17 | 2 | PHACTR3 | Intron | 20 |
| rs1041316 | SEQ ID NO: 18 | 1 | C14 orf101 | mRNA UTR | 14 |
| rs1416095 | SEQ ID NO: 19 | 1 | Between genes | Between genes | 1 |
| rs1020922 | SEQ ID NO: 20 | 1 | Between genes | Between genes | 5 |
| rs1583697 | SEQ ID NO: 21 | 1 | MGC57341 | Promoter | 12 |
| rs992922 | SEQ ID NO: 22 | 1 | PAPPA2 | mRNA UTR | 1 |
| rs566419 | SEQ ID NO: 23 | 1 | APC | mRNA UTR | 5 |
| rs1877290 | SEQ ID NO: 24 | 2 | BOMB | mRNA UTR | 4 |
| rs9875627 | SEQ ID NO: 25 | 2 | Between genes | Between genes | 3 |
| rs1741621 | SEQ ID NO: 26 | 1 | EEF1A2 | Locus region | 20 |
| rs310606 | SEQ ID NO: 27 | 1 | EEF1A2 | Intron | 20 |
| rs1504299 | SEQ ID NO: 28 | 2 | TAFA4 | mRNA UTR | 3 |
| rs12632390 | SEQ ID NO: 29 | 1 | Between genes | Between genes | 3 |
| rs1408889 | SEQ ID NO: 30 | 1 | DACH | Intron | 13 |
| rs225403 | SEQ ID NO: 31 | 1 | ABCG1 | Intron | 21 |

'Involved No. in multiple SNP combination' in Table 4 indicates how many times a single SNP was involved in the fourteen multiple SNP combinations (see Table 1).

'Gene' refers to a gene including the SNP.

'SNP function' indicates a role performed by a single SNP within the gene.

'No. of chromosome' indicates the number of chromosome at which a single SNP is positioned.

The multiple SNP according to the present embodiment may be one of fourteen multiple SNPs which are combinations of single SNPs. The combinations and the genotypes thereof are disclosed in Tables 2 and 3. 'Multiple SNP' in Table 3, indicates a combination of four selected single SNPs. 'Allele genotype' represents the allele bases in the single SNP positions in the order of SEQ ID NOS of the multiple SNP. For example, for No. 1 of Table 3, the allele genotype of rs1402026 is A1A2 or A2A2, the allele genotype of rs1177619 is A1A1, the allele genotype of rs 1191354 is A1A1 or A1A2, and the allele genotype of and rs731132 is A1A1 or A1A2.

In an embodiment of the present invention, a series of selections were made in order to find a combination of single SNPs, i.e. a multiple SNP, which correspond to a high incidence of colorectal cancer. The multiple SNP selection was performed using male subjects. After DNA was isolated from the blood of patients having colorectal cancer and normal persons and amplified, a specific SNP combination and the genotype thereof which were particularly shown in the patients, and not in normal persons, were identified. The identified SNP combinations and the genotype thereof are illustrated in Table 2 and 3. The characteristic of the multiple SNPs are described in Table 5 below.

tiple SNP or the multiple SNP of preceding No. among 295 inspected normal persons. Since many patients have two or more multiple SNPs, the cumulative appearance frequency is not linear. As indicated in Table 5, 177 among 247 patients have at least one of fourteen multiple SNPs.

'Odds ratio' indicates the ratio of the probability of the multiple SNP in the patient group to the probability of the multiple SNP in the normal group. That is, the odds ratio is ad/bc where a indicates the appearance frequency of the multiple SNP in the patient group, c indicates the appearance frequency of the multiple SNP in the normal group, b=[(total number of inspected patients)−a] and d=[(total number of normal unaffected men)−c]. The number of inspected patients and normal persons were respectively 247 and 295, and therefore b=[247−a] and d=[295−c].

If the odds ratio exceeds 1, there is an association between the multiple SNP and the patient group. The degree of the association increases with the odds ratio. As indicated in Table 5, the multiple SNP Nos. 1 through 14 according to an embodiment of the present invention have odds ratios ranging

TABLE 5

| No. | Cumulative appearance frequency of patient group | Cumulative appearance frequency of normal group | Appearance frequency of patent group | Appearance frequency of normal group |
|---|---|---|---|---|
| 1 | 27 | 1 | 27 | 1 |
| 2 | 32 | 2 | 27 | 1 |
| 3 | 33 | 3 | 28 | 2 |
| 4 | 35 | 3 | 30 | 3 |
| 5 | 60 | 7 | 31 | 4 |
| 6 | 70 | 10 | 29 | 4 |
| 7 | 77 | 14 | 31 | 5 |
| 8 | 79 | 16 | 32 | 6 |
| 9 | 106 | 24 | 33 | 8 |
| 10 | 124 | 32 | 33 | 8 |
| 11 | 139 | 39 | 35 | 9 |
| 12 | 148 | 47 | 35 | 9 |
| 13 | 161 | 58 | 40 | 13 |
| 14 | 177 | 68 | 46 | 19 |

| No. | Odds Ratio | 95% confidence interval | | 99% confidence interval | | Permutation test | | |
|---|---|---|---|---|---|---|---|---|
| | | | | | | Expected value (E) | Observed value (O) | Ratio (O/E) |
| 1 | 36.08 | 4.87 | 267.57 | 2.59 | 502.25 | 0.12 | 3 | 24.6 |
| 2 | 36.08 | 4.87 | 267.57 | 2.59 | 502.25 | 0.12 | 3 | 24.6 |
| 3 | 18.73 | 4.41 | 79.47 | 2.8 | 125.16 | 0.56 | 5 | 8.9 |
| 4 | 13.46 | 4.05 | 44.67 | 2.78 | 65.12 | 1.15 | 16 | 13.9 |
| 5 | 10.44 | 3.63 | 30.02 | 2.61 | 41.83 | 3.77 | 61 | 16.2 |
| 6 | 9.68 | 3.35 | 27.93 | 2.4 | 38.98 | 4.85 | 145 | 29.9 |
| 7 | 8.32 | 3.18 | 21.76 | 2.35 | 29.43 | 10.73 | 240 | 22.4 |
| 8 | 7.17 | 2.95 | 17.45 | 2.23 | 23.08 | 18.18 | 433 | 23.8 |
| 9 | 5.53 | 2.5 | 12.22 | 1.95 | 15.67 | 83.30 | 1,007 | 12.1 |
| 10 | 5.53 | 2.5 | 12.22 | 1.95 | 15.67 | 83.30 | 1,007 | 12.1 |
| 11 | 5.25 | 2.47 | 11.15 | 1.95 | 14.13 | 93.05 | 1,079 | 11.6 |
| 12 | 5.25 | 2.47 | 11.15 | 1.95 | 14.13 | 93.05 | 1,079 | 11.6 |
| 13 | 4.19 | 2.19 | 8.04 | 1.78 | 9.86 | 338.75 | 2,415 | 7.1 |
| 14 | 3.32 | 1.89 | 5.85 | 1.58 | 6.98 | 1,214.02 | 7,265 | 6.0 |

'No.' in Table 5 corresponds to No. in Table 2.

'Appearance frequency of patient group' refers to the number of patients having the multiple SNP among all 247 inspected patients. 'Appearance frequency of normal group' refers to the number of persons with the multiple SNPs among 295 inspected normal persons.

'Cumulative appearance frequency of patient group' refers to the number of patients having the corresponding multiple SNP or the multiple SNPs of preceding No. among all 247 inspected patients. 'Appearance frequency of normal group' refers to the number of persons with the corresponding mulbetween 3.32 and 36.08. Since the values are much greater than 1, it is estimated that there is a close association between the multiple SNP Nos. 1 through 14 according to an embodiment of the present invention and the incidence of colorectal cancer.

'95% confidence interval' or '99% confidence interval' indicates that there is 95% or 99% chance that the interval contains the actual odds ratio, and is obtained using the following formula. When 1 is within the confidence interval, i.e. the lower bound is below 1 and the upper bound is above 1, it is estimated that there is no association between the multiple SNP and the colorectal cancer.

95% confidence interval=(lower bound,upper bound)=
(odds ratio×exp(−1.960$\sqrt{V}$),odds ratio×exp(1.960$\sqrt{V}$)), where V=1/a+1/b+1/c+1/d).

99% confidence interval=(lower bound,upper bound)=
(odds ratio×exp(−2.576$\sqrt{V}$),odds ratio×exp(2.576$\sqrt{V}$)), where V=1/a+1/b+1/c+1/d).

'Permutation test' is performed to identify whether the odds ratio of the multiple SNP is accidentally determined value or actually has the value. 'Expected value (E)' indicates the expected number of genotype having odds ratio higher than the corresponding odds ratio. 'Observed value (O)' indicates the observed number of genotype having odds ratio higher than the corresponding odds ratio. 'Ratio (O/E)' indicates the ratio of the observed value to the expected value. If the ratio (O/E) is 1 or greater, it indicates that the analysis is significant. As can be seen from Table 5, multiple SNPs are proved to be significant.

The multiple SNP for colorectal cancer diagnosis according to an embodiment of the present invention may include one of the multiple SNPs, two or more of the multiple SNPs, for example, all of the multiple SNPs of Nos. 1 to 14.

The polynucleotides of the single SNPs included in the multiple SNP for colorectal cancer diagnosis may include at least 10 contiguous bases, for example, 10 to 100 contiguous bases.

A polynucleotide for colorectal cancer diagnosis according to another embodiment of the present invention can be hybridized with the polynucleotide or complementary polynucleotide thereof according to an embodiment of the present invention.

A microarray for colorectal cancer diagnosis according to another embodiment of the present invention includes the polynucleotide or the complementary nucleotide thereof, the polynucleotide hybridized with one of the polynucleotides, a polypeptide encoded by one of the polynucleotides or cDNA thereof according to an embodiment of the present invention.

According to an embodiment of the present invention, the microarray may be prepared using a conventional method known to those skilled in the art using the polynucleotide or the complementary polynucleotide thereof, the polynucleotide hybridized with the probe, the polypeptide encoded by one of the polynucleotides or cDNA thereof according to an embodiment of the present invention.

That is, the polynucleotide may be immobilized on a substrate coated with an active group selected among aminosilane, poly-L-lysine and aldehyde. Also, the substrate may be composed of a silicon wafer, glass, quartz, metal or plastic. The method of immobilizing the polynucleotide on the substrate may be either micropipetting using piezoelectric or a method using a pin-shaped spotter.

A kit for colorectal cancer diagnosis according to an embodiment of the present invention includes the microarray.

The kit may further include a primer set for isolating and amplifying DNA including the SNPs from the subjects. The appropriate primer set may be easily designed by those skilled in the art with reference to the sequences according to an embodiment of the present invention. For example, the primer set in Table 6 may be used.

A method of diagnosing colorectal cancer according to another embodiment of the present invention uses the multiple SNPs of the present invention.

The diagnosing method includes isolating DNA from a subject, determining a base sequence at a polymorphic site of the DNA, and judging that the subject has colorectal cancer or has a high incidence probability of colorectal cancer when the base sequence includes at least one of multiple SNPs in Table 3.

The DNA isolating may be carried out using a method known to those skilled in the art. For example, DNA can be directly purified from tissues or cells or a specific region can be amplified using a Polymerase Chain Reaction (PCR), etc. and isolated. In the description, DNA refers to not only DNA, but also cDNA synthesized from mRNA. Obtaining nucleic acids from a subject may be carried out by one of PCR amplification, ligase chain reaction (LCR) (Wu and Wallace, Genomics 4, 560 (1989), Landegren etc., Science 241, 1077 (1988)), transcription amplification (Kwoh etc., Proc. Natl. Acad. Sci. USA 86, 1173 (1989)), self-sustained sequence replication (Guatelli etc., Proc. Natl. Acad. Sci. USA 87, 1874 (1990)) and Nucleic Acid Sequence Based Amplification (NASBA).

Sequencing the isolated DNA may be performed through various methods known to those skilled in the art. For example, the nucleotides of nucleic acids may be directly sequenced using a dideoxy method. Also, the nucleotides of the polymorphic sites may be sequenced by hybridizing the DNA with a probe containing the sequence of the SNP site or a complementary probe thereof, and examining the degree of the hybridization. The degree of hybridization may be measured using a method of labeling the target DNA with a detectable label and specifically detecting the hybridized target, or using an electrical signal detecting method. The sequencing may include hybridizing DNA isolated from the subject with the microarray according to an embodiment of the present invention, washing to remove non-specific reaction, and examining a hybridization degree.

The subject is judged to have colorectal cancer or have a high incidence probability of colorectal cancer when at least one of the multiple SNPs in Table 3 is included in the nucleic acid isolated from the subject.

The present invention will now be described in greater detail with reference to the following examples. The following examples are for illustrative purposes only and are not intended to limit the scope of the invention.

EXAMPLE 1

Multiple SNP Selection

DNA samples were isolated from leucocytes in blood of a patient group with a colorectal cancer under treatment and a normal group without symptoms of colorectal cancer, and then an appearance frequency of a specific SNP was analyzed. The patient group and the normal group both consisted of Koreans. The SNPs of the Example were selected from either a published database (NCBI dbSNP:http://www.ncbi.nlm.nih.gov/SNP/) or a Sequenom website (http://www.realsnp.com/). The SNPs were analyzed using a primer close to the selected SNPs.

1-1. Preparation of DNA Sample

DNA was extracted from blood of a patient group consisting of 247 Korean patients with colorectal cancer under treatment and a normal group consisting of 295 Korean not having colorectal cancer symptoms (blood of the patient group: MyDNA (www.biobank, co.kr/korea/ma/mydna.shtml), blood of the normal group: Samsung Medical Center (www.smc.or.kr)). Chromosomal DNA extraction was carried out using a known molecular cloning extraction method (A Laboratory Manual, p 392, Sambrook, Fritsch and Maniatis, 2nd edition, Cold Spring Harbor Press, 1989) and guidelines of a commercially available kit (Gentra system, D-50K). Only DNA having a purity of at least 1.7, measured using UV (260/280 nm), was selected from the extracted DNA and used.

1-2. Amplification of the Target DNA

The target DNA having a certain DNA region including 85 SNPs to be analyzed was amplified using a PCR. The PCR was performed using a conventional method and the conditions were as indicated below. First, the chromosomal DNA was diluted to a concentration of 2.5 ng/ml. Then the following PCR mixture was prepared.

| | |
|---|---|
| Water (HPLC grade) | 2.24 μl |
| 10 × buffer (containing 15 mM MgCl$_2$, 25 mM MgCl$_2$) | 0.5 μl |
| dNTP mix (GIBCO) (25 mM/each) | 0.04 μl |
| Taq pol (HotStart) (5 U/μl) | 0.02 μl |
| Forward/reverse primer mix (1 μM/each) | 0.02 μl |
| DNA | 1.00 μl |
| Total volume | 5.00 μl |

The forward and reverse primers were selected upstream and downstream from the SNPs at proper positions in a known database. Several of the 85 primers are indicated in Table 6.

Thermal cycling of PCR was performed by maintaining the temperature at 95° C. for 15 minutes, cycling the temperature from 95° C. for 30 seconds, to 56° C. for 30 seconds to 72° C. for 1 minute a total of 45 times, maintaining the temperature at 72° C. for 3 minutes, and then storing at 4° C. As a result, target DNA fragments containing 200 nucleotides or less were obtained.

1-3. Analysis of SNP of the Amplified Target DNA

SNP analysis of the target DNA fragments was performed using a homogeneous Mass Extend (hME) technique from Sequenom. The principle of the hME technique is as follows. First, a primer, also called an extension primer, complementary to bases up to just before the SNP of the target DNA fragment was prepared. The primer was hybridized with the target DNA fragment and DNA polymerization was facilitated. At this time, added to the reaction solution was a reagent (Termination mix, e.g. ddTTP) for terminating the polymerization after the base complementary was added to a first allele base (e.g. 'A' allele) among the subject SNP alleles. As a result, when the target fragment DNA included the first allele (e.g. 'A' allele), a product containing only one base complementary to the first allele (e.g. 'T') added was obtained. On the other hand, when the target DNA fragment included a second allele (e.g. 'G' allele), a product having a base complementary to the second allele (e.g. 'C') extending to the first allele base (e.g. 'A') was obtained. The length of the product extending from the primer was determined using mass analysis to determine the type of allele in the target DNA. Specific experimental conditions were as follows.

First, free dNTPs were removed from the PCR product. To this end, 1.53 μl of pure water, 0.17 μl of an hME buffer, and 0.30 μl of shrimp alkaline phosphatase (SAP) were added to a 1.5 ml tube and mixed to prepare SAP enzyme solution. The tube was centrifuged at 5,000 rpm for 10 seconds. Then, the PCR product was put into the SAP solution tube, sealed, maintained at 37° C. for 20 minutes and at 85° C. for 5 minutes and then stored at 4° C.

Next, a homogeneous extension was performed using the target DNA product as a template. The reaction solution was as follows.

| | |
|---|---|
| Water (nanopure grade) | 1.728 μl |
| hME extension mix (10 × buffer containing 2.25 mM d/ddNTPs) | 0.200 μl |
| Extension primer (each 100 μM) | 0.054 μl |
| Thermosequenase (32 U/μl) | 0.018 μl |
| Total volume | 2.00 μl |

The reaction solution was mixed well and spin down centrifuged. A tube or plate containing the reaction solution was sealed and maintained at 94° C. for 2 minutes, cycled from 94° C. for 5 seconds, to 52° C. for 5 seconds to 72° C. for 5 seconds a total of 40 times, and then stored at 4° C. The obtained homogeneous extension product was washed with a resin (SpectroCLEAN, Sequenom, #10053) to remove a salt. Several of 85 extension primers used for homogeneous extension are disclosed in Table 6.

TABLE 6

| GenBank accession No. of SNP in NCBI | Primer for target DNA amplification (SEQ ID NO:) | | Extension primer (SEQ ID NO:) |
|---|---|---|---|
| | Forward primer | Reverse primer | |
| rs1402026 | 32 | 33 | 34 |
| rs1485217 | 35 | 36 | 37 |
| rs1177619 | 38 | 39 | 40 |
| rs1996489 | 41 | 42 | 43 |
| rs1334856 | 44 | 45 | 46 |
| rs2295706 | 47 | 48 | 49 |
| rs158240 | 50 | 51 | 52 |
| rs1191354 | 53 | 54 | 55 |
| rs1028586 | 56 | 57 | 58 |
| rs317913 | 59 | 60 | 61 |
| rs1486945 | 62 | 63 | 64 |
| rs1025882 | 65 | 66 | 67 |
| rs1511045 | 68 | 69 | 70 |
| rs954881 | 71 | 72 | 73 |
| rs731132 | 74 | 75 | 76 |
| rs1901223 | 77 | 78 | 79 |
| rs1182477 | 80 | 81 | 82 |
| rs1041316 | 83 | 84 | 85 |
| rs1416095 | 86 | 87 | 88 |
| rs1020922 | 89 | 90 | 91 |
| rs1583697 | 92 | 93 | 94 |
| rs992922 | 95 | 96 | 97 |
| rs566419 | 98 | 99 | 100 |
| rs1877290 | 101 | 102 | 103 |
| rs9875627 | 104 | 105 | 106 |
| rs1741621 | 107 | 108 | 109 |
| rs310606 | 110 | 111 | 112 |
| rs1504299 | 113 | 114 | 115 |
| rs12632390 | 116 | 117 | 118 |
| rs1408889 | 119 | 120 | 121 |
| rs225403 | 122 | 123 | 124 |

Mass analysis was performed on the obtained extension product to determine the sequence of a polymorphic site using Matrix Assisted Laser Desorption and Ionization-Time of Flight (MALDI-TOF). In the MALDI-TOF, a material to be analyzed was exposed to a laser beam and flew with an ionized matrix (3-Hydroxypicolinic acid) in a vacuum to a detector. The flying time to the detector was calculated to determine the mass. A light material can reach the detector in a shorter amount of time than a heavy material. The nucleotide sequences of SNPs in the target DNA may be determined based on differences in mass and known nucleotide sequences of the SNPs.

Determination results of nucleotide sequences of the SNPs of the target DNA using the MALDI-TOF are shown in Tables 1-3. Each allele may exist in the form of a homozygote or a heterozygote in a subject. According to Mendel's Law of inheritance and the Hardy-Weinberg Law, the genetic makeup of alleles constituting a population is maintained at a constant frequency. When the genetic makeup is statistically significant, it can be considered to be biologically meaningful. The SNPs according to embodiments of the present invention occur in colorectal cancer patients at a statistically significant level, and thus, can be efficiently used in the diagnosis of colorectal cancer.

1-4. Selection of Multiple SNP

A combination of SNPs, i.e., multiple SNPs, frequently found in the patients having colorectal cancer was selected based on the analyzed 85 SNP sequences of 247 patients having colorectal cancer and 295 normal persons.

First, it was determined that there are about $1.4 \times 10^9$ multiple SNPs composed of one to four of the 85 SNP sequences.

After the first screening, about 13,300 multiple SNPs having a genotype ratio of 2 or higher and a genotype difference of 0.1×(total number of patients) or higher were selected.

Genotype ratio=(number of patients having a certain genotype)/(number of normal persons having the genotype)

Genotype difference=(number of patients having a certain genotype)-(number of normal persons having the genotype)

In a second screening, odds ratio, 95% confidence interval and 99% confidence interval of the odds ratio were used. The odds ratio is defined as ad/bc, where a, b, c and d are defined in Table 7. If the odds ratio exceeds 1, it indicates that the genotype is associated with colorectal cancer.

TABLE 7

|  | Number of persons containing a certain multiple SNP genotype | Number of persons not containing a certain multiple SNP genotype |
| --- | --- | --- |
| Patent group frequency | a | b |
| Normal group frequency | c | d |

The 95% confidence interval of the odds ratio = (odds ratio × exp(−1.960√V), odds ratio × exp(1.960√V)) and the 99% confidence interval of the odds ratio = (odds ratio × exp(−2.576 √V), odds ratio × exp(2.576√V)), where V = 1/a + 1/b + 1/c + 1/d The selected 13,300 multiple SNPs, 9,819 multiple SNPs were selected by selecting the multiple SNPs having 1.5 or higher lower bound of the 95% confidence interval, selecting the multiple SNP having an odds ratio of 3.0 or higher, and then selecting the multiple SNPs having 1.5 or higher lower bound of 99% confidence interval. When the odds ratio and the lower bounds of the 95% and 99% confidence intervals exceed 1.0, the results are statistically significant. However, the required standards were set to 1.5, 3.0 and 1.5 respectively in order to select the most effective markers.

Among the 9,819 multiple SNPs, fourteen multiple SNPs, which are composed of small number of single SNPs, having a high odds ratio, that is, high coverage for the patient group and low coverage for the normal group, were selected using a Greedy method (Cormen et al., "Introduction to Algorithms", MIT Press, 2001) which is an optimizing methods. The fourteen multiple SNPs are disclosed in Table 1.

EXAMPLE 2

Preparation of SNP Immobilized Microarray

A microarray was prepared by immobilizing the selected SNPs on a substrate. That is, multiple SNPs of Nos. 1 through 14 in Table 2 which is a combination of one or more polynucleotides including 20 contiguous nucleotides selected from polynucleotides in Table 1 and including the $101^{st}$ base, in which the SNPs were positioned at the $11^{st}$ nucleotide and the allele genotype of $101^{st}$ base of the selected polynucleotides was as illustrated in Table 3, were immobilized on the substrate.

First, N-ends of each of the polynucleotides were substituted with an amine group and the polynucleotides were spotted onto a silylated slide (Telechem) where 2×SSC (pH 7.0), a spotting buffer, was used. After the spotting, binding was induced in a drying machine and free oligonucleotides were removed by washing with 0.2% SDS for 2 minutes and with triple distilled water for 2 minutes. The microarray was prepared using denaturation induced by increasing the temperature of the slide to 95° C. for 2 minutes, washing with a blocking solution (1.0 g $NaBH_4$, PBS (pH 7.4) 300 mL, EtOH 100 mL) for 15 minutes, a 0.2% SDS solution for 1 minute and triple distilled water for 2 minutes, and then drying at room temperature.

EXAMPLE 3

Diagnosis of Colorectal Cancer Using the Microarray

A target DNA was isolated from the blood of the subject to diagnose the incidence or possibility of colorectal cancer and labeled was with a fluorescent material using the method described in Examples 1-1 and 1-2. The fluorescent labeled target DNA was hybridized with the microarray prepared in Example 2 at 42° C. for 4 hours in UniHyb hybridization solution (TeleChem). The slide was washed twice with 2×SSC at room temperature for 5 minutes and dried in air. The dried slide was scanned using a ScanArray 5000 (GSI Lumonics). The scanned results were analyzed using a QuantArray (GSI Lumonics) and ImaGene software (BioDiscover). The probability of incidence of colorectal cancer and the susceptibility thereto were measured by identifying whether the subject had a partial or whole multiple SNP according to an embodiment of the present invention.

The SNP according to the present invention can be used to effectively diagnose the incidence or the incidence probability of colorectal cancer.

While the present invention has been particularly shown and described with reference to exemplary embodiments thereof, it will be understood by those of ordinary skilled in the art that various changes in form and details may be made therein without departing from the spirit and scope of the present invention as defined by the following claims.

The invention claimed is:

1. A set of polynucleotides for colorectal cancer diagnosis including
polynucleotides of at least 25 contiguous bases of SEQ ID NOS: 1 (rs1402026), 3 (rs1177619), 8 (rs1191354), and 15 (rs731132) wherein the 25 contiguous bases include the 101st base, or complementary polynucleotides thereof,
and optionally at least one polynucleotide of at least 25 contiguous bases of a sequence selected from the group consisting of SEQ ID NOS: 2, 4-7, 9-14, and 16-31 wherein the 25 contiguous bases include the 101st base of the sequence, or a complementary polynucleotide thereof.

2. The set of polynucleotides of claim 1, consisting of polynucleotides of at least 25 contiguous bases of SEQ ID NOS: 1-31 wherein the 25 contiguous bases include the 101st base, or complementary polynucleotides thereof.

3. The set of polynucleotides of claim 1, wherein the polynucleotides comprise no more than 100 contiguous bases.

4. A set of polynucleotides hybridized with the set of polynucleotides of claim 1.

5. A microarray for colorectal cancer diagnosis comprising the set of polynucleotides of claim 4.

6. A microarray for colorectal cancer diagnosis comprising the set of polynucleotides of claim 1.

7. The microarray of claim 6, wherein the polynucleotides are immobilized on a substrate coated with an active group selected from the group consisting of amino-silane, poly-L-lysine and aldehyde.

8. The microarray of claim 7, wherein the substrate is composed of a material selected from the group consisting of silicon wafer, glass, quartz, metal and plastic.

9. A kit for colorectal cancer diagnosis comprising the microarray of claim 6.

* * * * *